United States Patent
Millar

(10) Patent No.: US 11,400,208 B2
(45) Date of Patent: Aug. 2, 2022

(54) MULTIPURPOSE UTILITY HOLDER FOR IV POLE

(71) Applicant: Allen Currie Millar, Rogers, AR (US)

(72) Inventor: Allen Currie Millar, Rogers, AR (US)

( * ) Notice: Subject to any disclaimer, the term of this patent is extended or adjusted under 35 U.S.C. 154(b) by 21 days.

(21) Appl. No.: 17/065,770

(22) Filed: Oct. 8, 2020

(65) Prior Publication Data
US 2022/0111141 A1     Apr. 14, 2022

(51) Int. Cl.
*A61M 5/14*     (2006.01)

(52) U.S. Cl.
CPC ........ *A61M 5/1417* (2013.01); *A61M 5/1415* (2013.01); *A61M 2209/082* (2013.01)

(58) Field of Classification Search
CPC .............. A61M 5/1415; A61M 5/1417; A61M 5/1414; A61M 2209/082; F16B 2/22; F16B 2/243; F16B 7/1445; F16B 7/1427; F16B 2/1418; A61G 7/0503; F16M 13/02; F16M 13/022; F16M 11/26
USPC ............ 248/158, 219.1, 230.7, 219.4, 218.4, 248/222.52, 297.51
See application file for complete search history.

(56) References Cited

U.S. PATENT DOCUMENTS

| | | | |
|---|---|---|---|
| 1,799,079 A * | 3/1931 | Bemis | A47K 1/02 248/312.1 |
| 2,486,276 A * | 10/1949 | Guy | D06F 53/04 24/129 R |
| 4,702,448 A | 10/1987 | LoJacono | |
| 4,821,988 A * | 4/1989 | Jimenez | A61G 7/0503 D8/395 |
| 4,953,819 A | 9/1990 | Davis | |
| 5,351,920 A * | 10/1994 | Decky | F16L 3/13 248/74.1 |
| 5,358,205 A * | 10/1994 | Starkey | F16B 7/0493 248/220.21 |
| 5,588,166 A | 12/1996 | Burnett | |
| 6,409,131 B1 | 6/2002 | Bentley et al. | |
| 6,588,716 B1 * | 7/2003 | Heid | F16M 13/02 248/161 |
| 6,802,484 B1 * | 10/2004 | Kiley | A47G 23/0225 248/311.2 |
| 6,969,031 B2 * | 11/2005 | Ugent | A61M 5/1415 248/129 |
| 7,111,812 B2 * | 9/2006 | Shannon | H04M 1/04 248/227.3 |
| 7,533,854 B2 | 5/2009 | Aube | |
| 8,348,072 B2 * | 1/2013 | Whitehall | A47B 96/1425 248/408 |
| D678,533 S | 3/2013 | Bernstein | |
| 9,179,208 B2 * | 11/2015 | Hilderman | H04R 1/025 |
| 9,198,727 B1 * | 12/2015 | Samuels | A61F 15/001 |

(Continued)

FOREIGN PATENT DOCUMENTS

CN          111420161          7/2020

OTHER PUBLICATIONS

European Search Report for European Application No. 21203989.5-1122; dated Apr. 4, 2022.

*Primary Examiner* — Ingrid M Weinhold
(74) *Attorney, Agent, or Firm* — Dennis D. Brown; Brown Patent Law, P.L.L.C.

(57) ABSTRACT

A cleanable and reusable device which is attachable on an IV pole for holding multiple different instruments and articles such as an ether screen, a pacemaker, additional IV bags, and/or a transesophageal echo probe.

14 Claims, 5 Drawing Sheets

(56) References Cited

U.S. PATENT DOCUMENTS

| | | | |
|---|---|---|---|
| 9,291,305 B2* | 3/2016 | Brehm | A61B 50/20 |
| 10,190,609 B2 | 1/2019 | Turturro et al. | |
| 10,264,736 B2* | 4/2019 | Rider | A01G 9/12 |
| 11,123,617 B2* | 9/2021 | Fulford | B60R 9/08 |
| 2005/0116126 A1* | 6/2005 | Ugent | A61M 5/1415 |
| | | | 248/129 |
| 2008/0011907 A1 | 1/2008 | Jacobsma | |
| 2013/0181100 A1* | 7/2013 | Blankenship | A61M 5/1415 |
| | | | 248/129 |
| 2014/0209550 A1 | 7/2014 | Pryor et al. | |
| 2014/0259557 A1 | 9/2014 | Egan | |
| 2015/0115123 A1* | 4/2015 | Ng | A47B 19/002 |
| | | | 248/462 |
| 2015/0157522 A1 | 6/2015 | Blankenship et al. | |
| 2018/0128421 A1* | 5/2018 | Hilderman | F16B 2/22 |
| 2018/0335177 A1* | 11/2018 | Black | F16G 11/101 |

\* cited by examiner

MULTIPURPOSE UTILITY HOLDER FOR IV POLE

FIELD OF THE INVENTION

The present invention relates to devices for holding articles, such as (i) additional IV bags, bottles or other containers for intravenous fluid therapies, (ii) pacemakers, (iii) ether screens, (iv) transesophageal echo probes, and/or (v) other articles, on IV poles.

BACKGROUND OF THE INVENTION

IV poles are used in operating rooms, cardiac catheterization labs, endoscopic labs, intensive care units, and in other medical treatment areas and facilities for hanging fluid bags, bottles, and other containers for intravenous therapies. In addition, various makeshift devices have also been used on IV poles for hanging pacemakers, ether screens (which shield the anesthesia personnel from the surgical field), transesophageal echo probes, and other articles.

Unfortunately, the makeshift devices heretofore used in the art for holding other articles on IV poles have been deficient in many important respects. Typically, the ether screen has been held by a simple clip and the pacemaker has been hung by a homemade hook formed by bending a stylet (i.e., a soft metal rod). In addition to being unstable, the homemade book holds the pacemaker up high at a point above the ether screen so that the pacemaker is exposed to blood and other contaminants from the surgical field. Moreover, the stylet, which can only be used once, must be thrown away after just a single use.

Consequently, a need exists for an improved device for holding an ether screen, a pacemaker, transesophageal echo probes, and other articles on an IV pole. The device will preferably hold the pacemaker and other articles in a more secure manner and will preferably position the pacemaker behind, rather than above, the ether screen so that the pacemaker is shielded from the surgical field. The improved device will also preferably be cleanable and reusable. In addition, the improved device will preferably allow additional IV fluid bags, bottles, or other containers to be hung from the IV pole.

SUMMARY OF THE INVENTION

The present invention provides a multipurpose utility holder for an IV pole which satisfies the needs and alleviates the problems discussed above. The inventive multipurpose holder is cleanable and reusable and can be used to securely hold multiple different types of articles on an IV pole in a much safer and more stable manner. Examples of such articles include but are not limited to (i) additional IV bags, bottles, or other containers for intravenous fluid therapies, (ii) pacemakers, (iii) ether screens, and (iv) transesophageal echo probes. The multipurpose utility holder will also position articles such as pacemakers behind, rather than above, the ether screen so that they are shielded from the surgical field.

In one aspect, there is provided a utility holder for an IV pole. The utility holder preferably comprises: (i) a longitudinal axis; (ii) an open lower collar which extends from about 190° to about 320° around the longitudinal axis, the open lower collar having a lateral cross-sectional C-shape; (iii) an open upper collar which extends from about 190° to about 320° around the longitudinal axis, the open upper collar being positioned longitudinally above the open lower collar and the open upper collar having a lateral cross-sectional C-shape; and (iv) a connecting arm which extends longitudinally from the open lower collar to the open upper collar.

In another aspect, there is provided a utility holder which preferably comprises: (i) a longitudinal axis; (ii) an open collar which extends from about 190° to about 320° around the longitudinal axis, the open collar having a flexible side gap opening and the open collar having a lateral cross-sectional C-shape; (iii) the open collar having a retaining shoulder at an upper longitudinal end of the open collar which extends radially inward toward the longitudinal axis; (iv) the retaining shoulder extending from about 190° to about 320° around the longitudinal axis: and (v) a plurality of holding structures which project outwardly from the open collar. The utility holder can also comprise (a) an IV pole apparatus comprising a lower pole segment, an upper pole segment which telescopingly extends through an upper end of the lower pole segment, and a locking collar on the upper end of the lower pole segment for locking the upper pole segment at a selected height and (b) the locking collar of the IV pole apparatus being received in the open collar such that the retaining shoulder of the open collar rests on the locking collar.

Further aspects, features and advantages of the present invention will be apparent to those in the art upon examining the accompanying drawings and upon reading the following Detailed Description of the Preferred Embodiments.

DETAILED DESCRIPTION OF THE PREFERRED EMBODIMENTS

Figure 1:
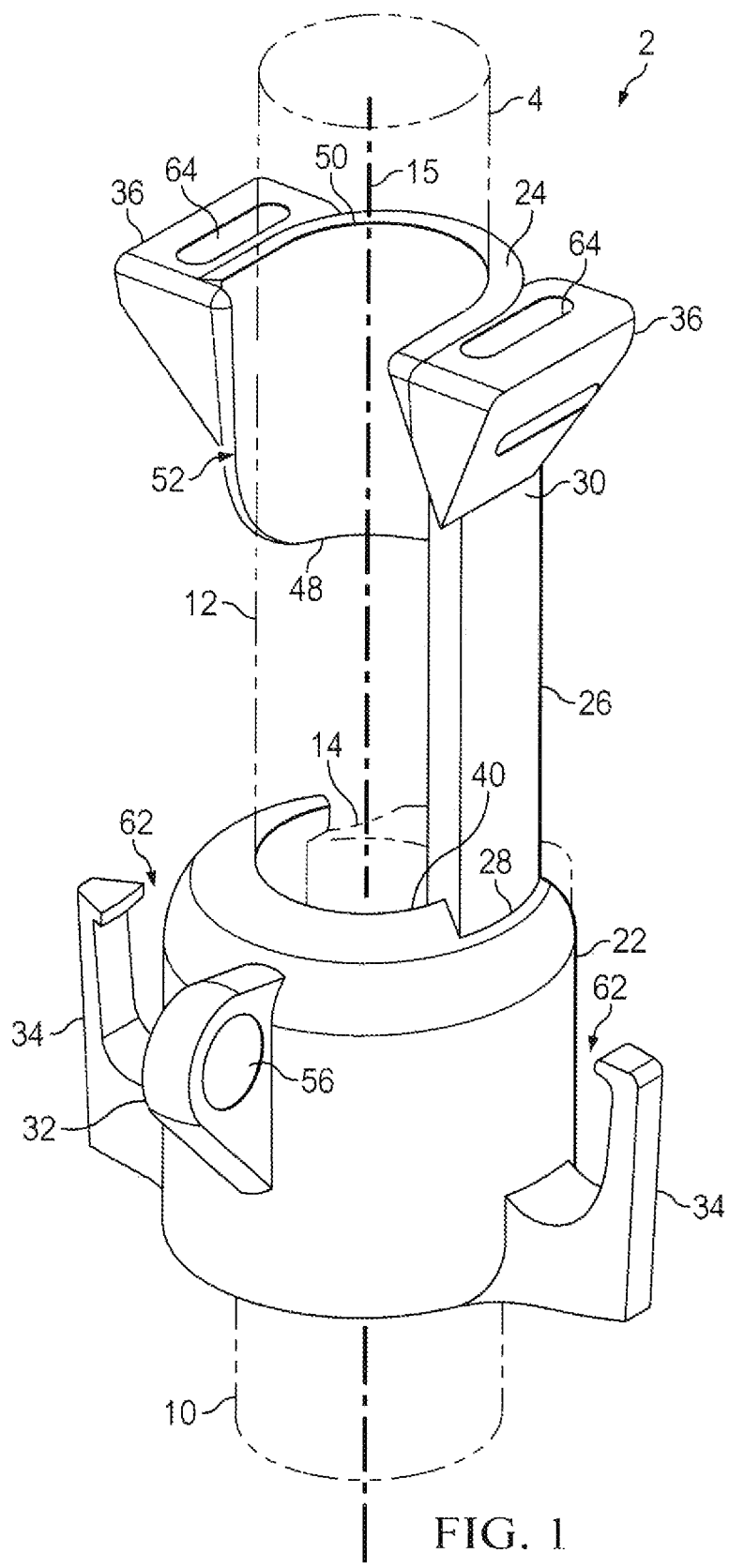
FIG. 1 is a perspective view of an embodiment 2 of the inventive multipurpose utility holder.
Figure 2:
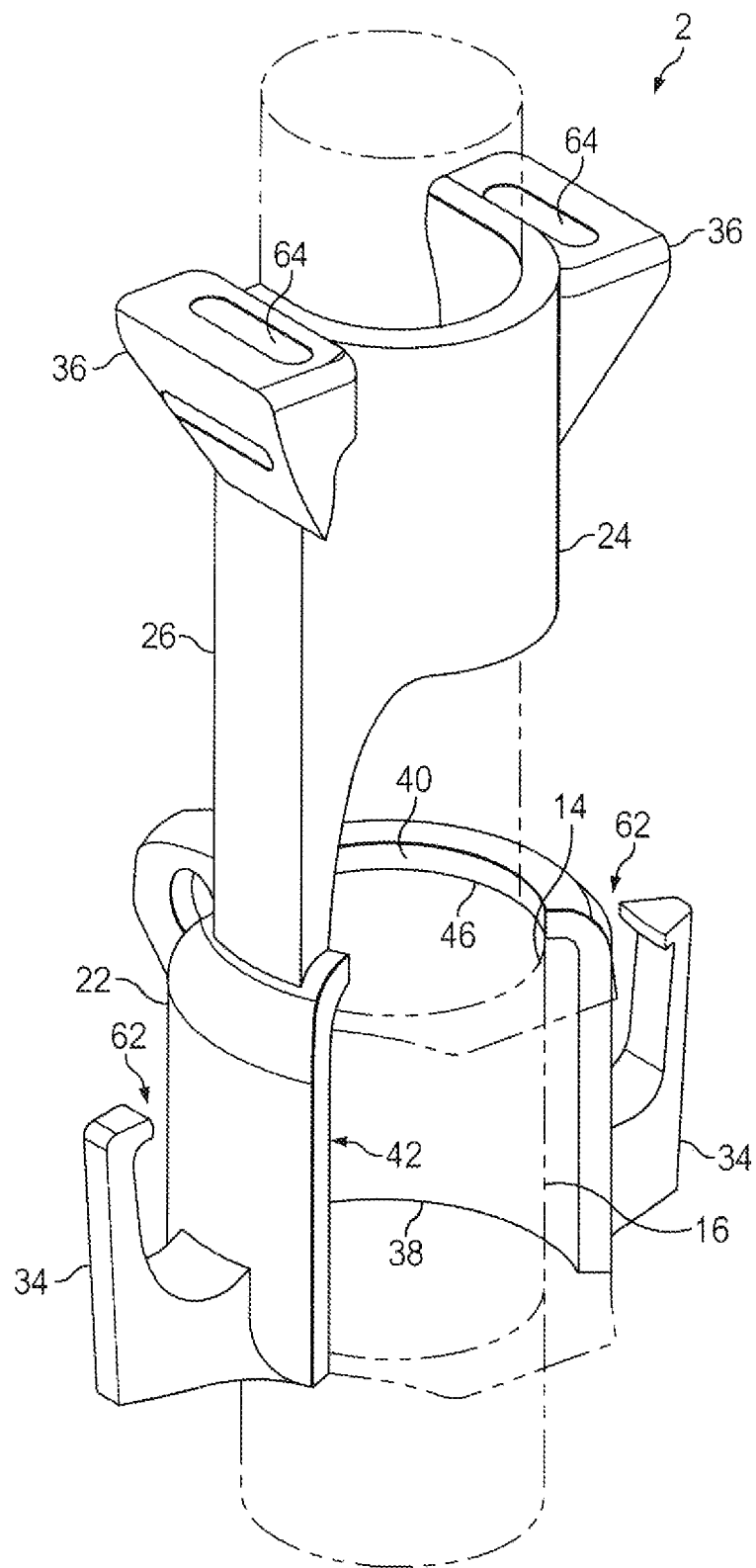
FIG. 2 is another perspective view of the inventive utility holder 2.
Figure 3:
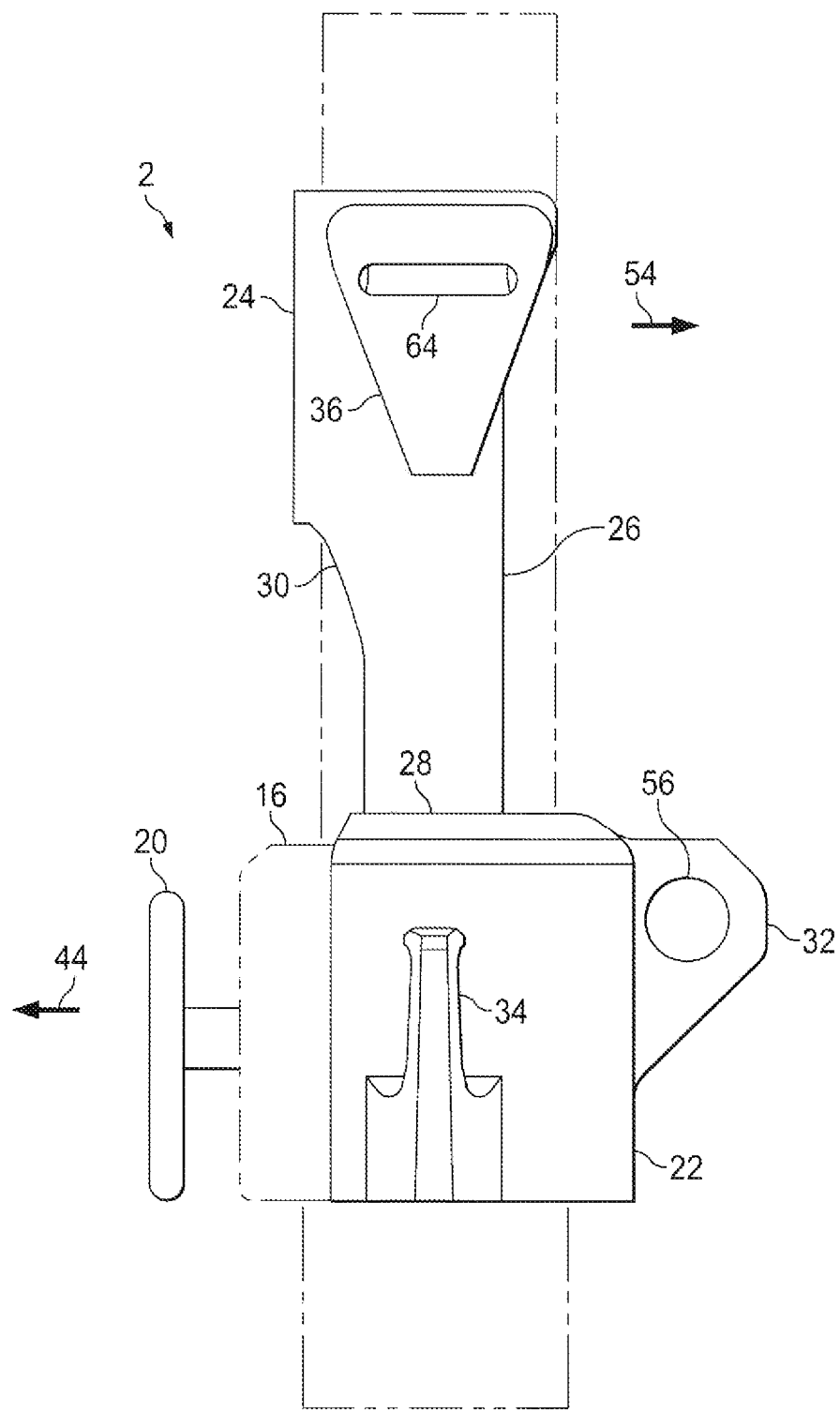
FIG. 3 is an elevational side view of the inventive utility holder 2.
Figure 4:
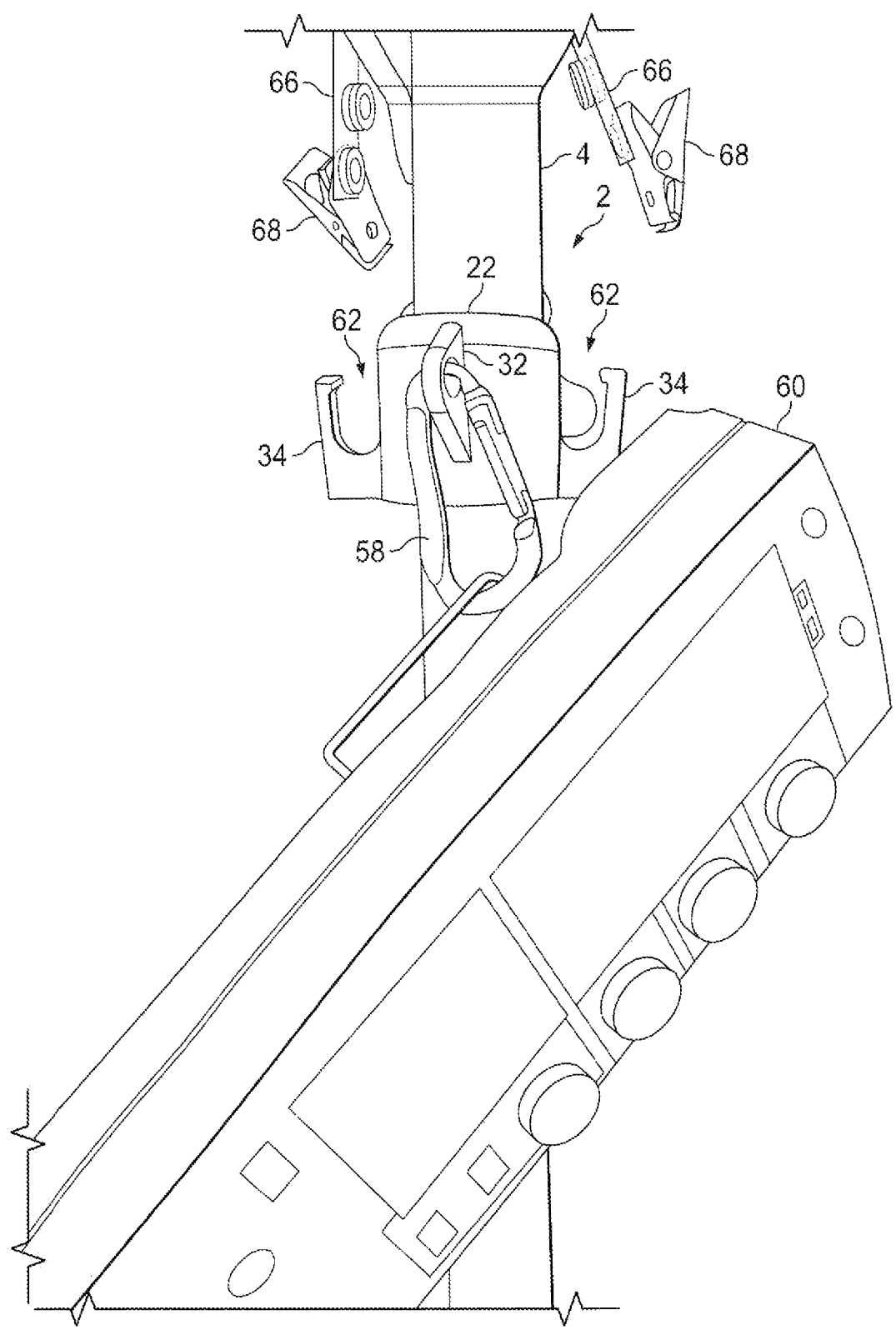
FIG. 4 is another devotional view of the inventive utility holder 2.

An embodiment 2 of the inventive multipurpose utility holder is shown in FIGS. 1-4. As illustrated in FIGS. 1-4, the multipurpose holder 2 is removably secured on an IV pole apparatus 4. The IV pole apparatus 4 can be any type of IV pole apparatus which is known in the art. The IV pole apparatus 4 will typically comprise: a weighted base with wheels (not shown); a lower pole segment 10 which extends upwardly from the weighted base; an upper pole segment 12 which is slideably received in the lower pole segment 10 so that the upper pole segment telescopingly extends upwardly through the upper end 14 of the lower pole segment 10; a locking collar 16 on the upper end 14 of the lower pole segment 10 for releasably locking the upper pole segment 12 at a desired height selected by the user; and a set of hooks at the top of the upper pole segment 12 for hanging bags, bottles, or other containers containing fluids used for intravenous medical therapies. The locking collar 16 can be (a) a knob-type collar which comprises a locking bolt which extends radially through the collar 16 and has a hand knob 20 on the outer end thereof for tightening and releasing the locking collar 16, (b) a twist-type collar which is threadedly received on the upper end 14 of the lower pole segment 10, or (c) any other type of locking collar device used in the art.

The multipurpose utility holder 2 preferably comprises: a longitudinal axis 15; an open lower collar 22 in which the locking collar 16 of the IV pole 4 is removably received; an open upper collar 24 through which the upper pole segment 12 of the IV pole 4 is removably received; a longitudinally extending connecting arm 26 having a lower end 28 which is connected to the open lower collar 22 and an upper end 30 which is connected to the open upper collar 24; one or more attachment structures 32, 34 which project from the open lower collar 22; and one or more attachment structures 36 which project from the open upper collar 24.

Although other fabrication techniques can alternatively be used, the multipurpose utility holder 2 is preferably a unitary molded structure which is formed of a non-porous plastic material. The plastic material will preferably be both (a) sufficiently flexible for placing the inventive utility holder 2 on the IV pole apparatus 4 and (b) sufficiently resilient for tightly gripping the IV pole 4 when the utility holder 2 is in use for holding multiple articles.

The open lower collar 22 of the inventive utility holder 2 has an open lower end 38 and open upper end 40. The open lower collar 22 also has a lateral cross-sectional C-shape such that the open lower collar 22 has a side gap opening 42 which faces in a first radial direction 44. The open lower collar 22 preferably extends from about 190° to about 320° (i.e., within±5°) around both (i) the longitudinal axis 15 of the inventive holder 2 and (ii) the IV pole 4. The open lower collar 22 more preferably extends at least 200° and most preferably extends from about 220° to about 280° around the longitudinal axis 15 and the IV pole 4.

The material used for forming the inventive utility holder 2 will preferably allow the side gap opening 42 of the open lower collar 22 to flex to a degree which is sufficient for receiving at least the upper pole segment 12 of the IV pole 4 for placing the open lower collar 22 on the locking collar 16.

The open lower collar preferably also includes a retaining shoulder 46, located at the upper longitudinal end 40 of the lower collar 22, which rests on the upper end of the locking collar 16 of the IV pole 4 when the locking collar 16 is received in open lower collar 22. The retaining shoulder 46 extends radially inward toward the longitudinal axis 15 and is preferably an inwardly curved shoulder. As with the remainder of the open lower collar 22, the retaining, shoulder 46 preferably extends from about 190° to about 320°, more preferably at least 200° and more preferably from about 220° to about 280°, around the longitudinal axis 15.

The open upper collar 24 of the inventive utility holder 2 has an open lower end 48 and open upper end 50. The open upper collar 24 also has a lateral cross-sectional C-shape such that the open upper collar 24 has a side gap opening 52 which laces in a second radial direction 54. The open upper collar 24 preferably extends from about 190° to about 320° (i.e., within±5°) around both (i) the longitudinal axis 15 of the inventive holder 2 and (ii) the IV pole 4. The open upper collar 24 more preferably extends at least 200° and most preferably extends from about 220° to about 280° around the longitudinal axis 15 and the IV pole 4.

The material used for forming the inventive utility holder 2 will preferably allow the side gap opening 52 of the open upper collar 24 to flex to a degree which is sufficient for receiving the upper pole segment 12 of the IV pole 4 to place the open upper collar 24 on the upper pole segment 12.

As noted above, the side gap opening 42 of the open lower collar 22 faces in a first radial direction 44 and the side gap opening 52 of the open upper collar 24 faces in a second radial direction 54. The second radial direction 54 is preferably different from the first radial direction 44 and is more preferably about 180° opposite the first radial direction 44. In addition, the connecting arm 26 of the inventive multipurpose utility holder 2 preferably extends longitudinally along only one side of the utility holder 2 and does not block or interfere with either the side gap opening 42 of the open lower collar 22 or the side gap opening 52 of the open upper collar 24. This configuration allows the inventive utility holder 2 to be snapped onto the IV pole apparatus 4 without disassembling the IV pole 4.

The one or more attachment structures 32, 34 which project outwardly from the open lower collar 22 of the multipurpose utility holder 2 and the one or more attachment structures 36 which project outwardly from the open upper collar 24 can be any type of structures suitable for holding instruments, screens (e.g., drapes), lubes, probes, additional IV bags, and/or other articles on the IV pole 4 for use in a surgical operating room, a cardiac catheterization lab, an endoscopic lab, an intensive care unit, or other medical treatment area or facility.

At least one of the attachment structures provided on the open lower collar 22 is preferably an ear-shaped attachment lug 32 having an aperture 56 extending therethrough for, e.g., receiving and holding a carabiner 58 for attaching a pacemaker 60 or other instrument to the open lower collar 22. Alternatively, or in addition, at least one, preferably two, of the attachment structures on the open lower collar 22 is/are hook structure(s) 34. Each hook 34 preferably has an upper opening 62 and will receive and hold, e.g., an IV bag or a transesophageal echo probe.

At least one, preferably two, of the attachment structures provided on the open upper collar 24 is/are attachment lug(s) 36, each of which has a slot 64 extending therethrough, e.g., for receiving and holding a band 66 of a band clip 68 for attaching an ether screen to the open upper collar 24.

Figure 5:
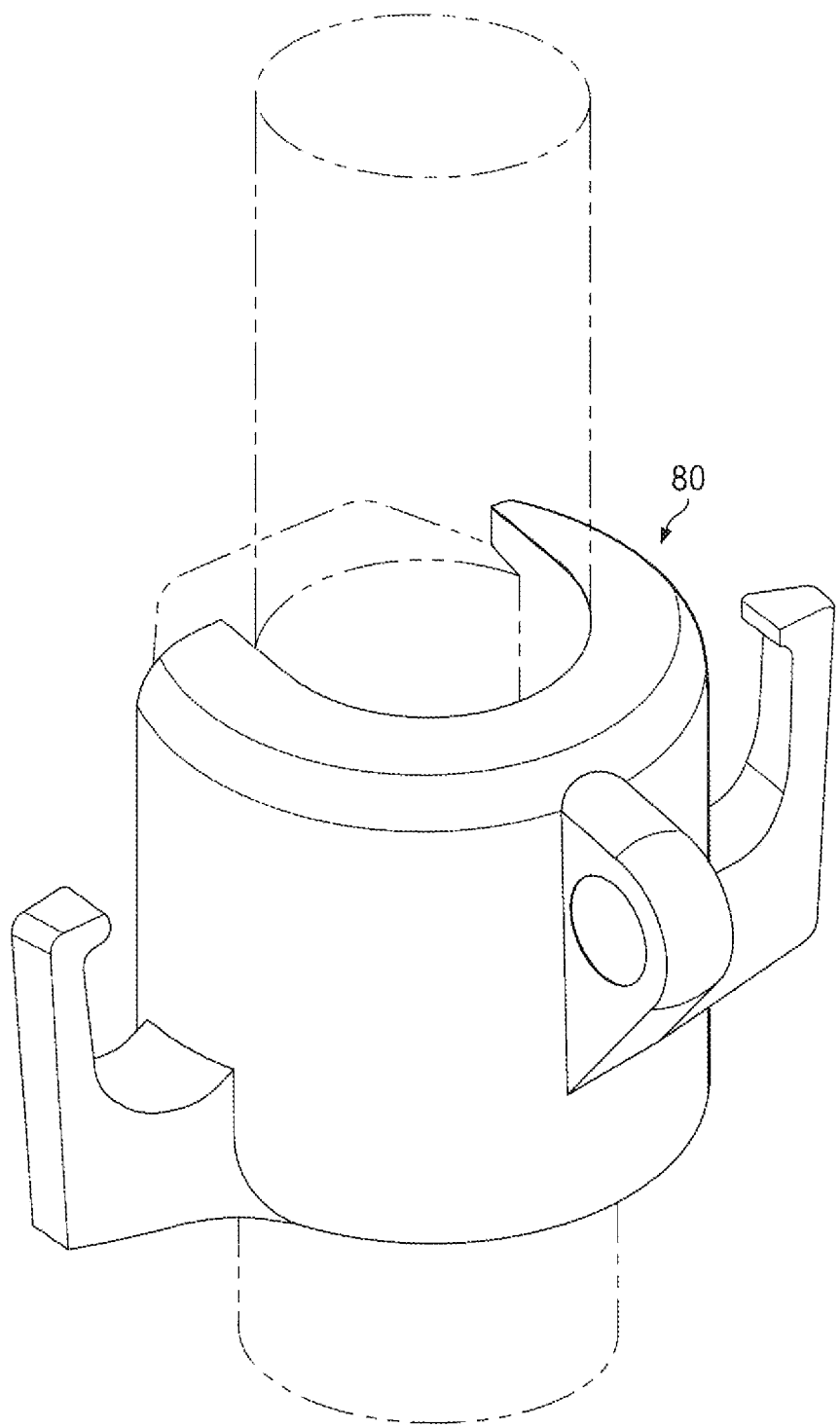
FIG. 5 is a perspective view of an alternative embodiment 80 of the inventive, multipurpose utility bolder.

An alternative embodiment 80 of the inventive multipurpose utility holder is illustrated in FIG. 5. The inventive utility holder 80 is identical to the inventive utility holder 2 except that the utility holder 80 does not include the open upper collar 24 of the inventive holder 2 and does not include the connecting arm 26 of the holder 2 which extends between the open lower collar 22 and the open upper collar 24.

Thus, the present invention is well adapted to carry out the objects and attain the ends and advantages mentioned above as well as those inherent therein. While presently preferred embodiments have been described for purposes of this disclosure, numerous changes and modifications will be apparent to those in the art. Such changes and modifications are encompassed within this invention as defined by the claims.

What is claimed is:

1. A utility holder for an IV pole, the utility holder comprising:
   a longitudinal axis;
   an open lower collar which extends from about 190° to about 320° around the longitudinal axis, the open lower collar having a lateral cross-sectional C shape;
   an open upper collar which extends from about 190° to about 320° around the longitudinal axis, the open upper collar being positioned longitudinally above the open lower collar and the open upper collar having a lateral cross-sectional C-shape;
   a connecting arm which extends longitudinally from the open lower collar to the open upper collar;

the open lower collar having a flexible side gap opening;
the open upper collar having a flexible side gap opening;
the flexible side gap opening of the open lower collar facing a first radial direction with respect to the longitudinal axis;
the flexible side gap opening of the open upper collar facing a second radial direction with respect to the longitudinal axis which is different from the first radial direction;
the open lower collar having a retaining shoulder at an upper longitudinal end of the open lower collar which extends radially inward toward the longitudinal axis; and
the retaining shoulder being an inwardly curved shoulder.

2. The utility holder of claim 1 further comprising the second radial direction being about 180° opposite, the first radial direction.

3. The utility holder of claim 1 further comprising an attachment lug projecting outwardly from the open lower collar, the attachment lug having an aperture extending therethrough.

4. The utility holder of claim 3 further comprising a carabiner attached to the open lower collar through the aperture of the attachment lug.

5. The utility holder of claim 1 further comprising one or more hooks which extend outwardly from the open lower collar.

6. The utility holder of claim 5 further comprising each of the one or more hooks having an upper opening.

7. The utility holder of claim 1 further comprising one or more attachment lugs which project outwardly from the open upper collar, each of the one or more attachment lugs having a slot extending therethrough.

8. The utility holder of claim 7 further comprising the slot of at least one of the one or more attachment lugs having a band of a band clip extending therethrough.

9. An IV apparatus comprising:
a utility holder comprising
a longitudinal axis;
an open lower collar which extends from about 190° to about 320° around the longitudinal axis, the open lower collar having a flexible side gap opening and the open lower collar having a lateral cross-sectional C-shape;
the open lower collar having a retaining shoulder at an upper longitudinal end of the open lower collar which extends radially inward toward the longitudinal axis;
the retaining shoulder extending from about 190° to about 320° around the longitudinal axis;
a plurality of holding structures which project outwardly from the open lower collar;
an open upper collar which extends from about 190° to about 320° around the longitudinal axis, the open upper collar being positioned longitudinally above the open lower collar and the open upper collar having a lateral crass-sectional C-shape;
a connecting arm which extends longitudinally from the open lower collar to the open upper collar;
the open upper collar having a flexible side gap opening;
the flexible side gap opening of the open lower collar facing a first radial direction with respect to the longitudinal axis;
the flexible side gap opening of the open upper collar facing a second radial direction with respect to the longitudinal axis which is different from the first radial direction; and
one or more holding structures which project outwardly from the open upper collar;
an IV pole comprising a lower pole segment, an upper pole segment which telescopingly extends through an upper end of the lower pole segment, and a locking collar on the upper end of the lower pole segment for locking the upper pole segment at a selected height;
the locking collar of the IV pole being received in the open lower collar such that the retaining shoulder of the open lower collar rests on the locking collar; and
the upper pole segment of the IV pole being received through the open upper collar.

10. The IV apparatus of claim 9 further comprising at least one of the holding structures being an attachment lug having an aperture extending therethrough.

11. The TV apparatus of claim 10 further comprising a carabiner attached to the open collar through the aperture of the attachment lug.

12. The IV apparatus of claim 9 further comprising at least one of the holding structures being a hook having an upper opening.

13. The IV apparatus of claim 9 further comprising:
the one or more holding structures which project outwardly from the open upper collar comprising at least one attachment lug having a slot extending therethrough and
the utility holder further comprising the slot of the at least one attachment lug having a band of a band clip extending therethough.

14. A utility holder for an IV pole, the utility holder comprising:
a longitudinal axis;
an open lower collar which extends from about 190° to about 320° around the longitudinal axis, the open lower collar having a lateral cross-sectional C-shape;
an open upper collar which extends from about 190° to about 320° around the longitudinal axis, the open upper collar being positioned longitudinally above the open lower collar and the open upper collar having a lateral cross-sectional C-shape;
a connecting arm which extends longitudinally from the open lower collar to the open upper collar;
the open lower collar having a retaining shoulder at an upper longitudinal end of the open lower collar which extends radially inward toward the longitudinal axis; and
the retaining shoulder extending from about 190° to about 320° around the longitudinal axis;
the open lower collar having a flexible side gap opening;
the open upper collar having a flexible side gap opening;
the flexible side gap opening of the open lower collar facing a first radial direction with respect to the longitudinal axis; and
the flexible side gap opening of the open upper collar facing a second radial direction with respect to the longitudinal axis which is different from the first radial direction.

\* \* \* \* \*

UNITED STATES PATENT AND TRADEMARK OFFICE
CERTIFICATE OF CORRECTION

| | |
|---|---|
| PATENT NO. | : 11,400,208 B2 |
| APPLICATION NO. | : 17/065770 |
| DATED | : August 2, 2022 |
| INVENTOR(S) | : Allen Currie Millar |

It is certified that error appears in the above-identified patent and that said Letters Patent is hereby corrected as shown below:

In the Claims

Claim 1, Column 4, Line 60: Replace the word "C shape" with "C-shape"

Claim 9, Column 5, Line 57: Replace the words "crass-sectional" with "cross-sectional"

Signed and Sealed this
Twenty-fifth Day of October, 2022

*Katherine Kelly Vidal*

Katherine Kelly Vidal
*Director of the United States Patent and Trademark Office*